US006864062B2

(12) United States Patent
Zinkowski et al.

(10) Patent No.: US 6,864,062 B2
(45) Date of Patent: Mar. 8, 2005

(54) PURIFIED ANTIGEN FOR ALZHEIMER'S DISEASE AND METHODS OF OBTAINING AND USING SAME

(75) Inventors: Raymond P. Zinkowski, Northbrook, IL (US); Daniel J. Kerkman, Lake Villa, IL (US); Russell E. Kohnken, Skokie, IL (US); John F. DeBernardis, Lindenhurst, IL (US); Peter Davies, Rye, NY (US)

(73) Assignee: Molecular Geriatrics Corporation, Vernon Hills, IL (US)

( * ) Notice: Subject to any disclaimer, the term of this patent is extended or adjusted under 35 U.S.C. 154(b) by 189 days.

(21) Appl. No.: 10/017,822

(22) Filed: Dec. 12, 2001

(65) Prior Publication Data

US 2003/0113896 A1 Jun. 19, 2003

Related U.S. Application Data

(63) Continuation of application No. 09/334,582, filed on Jun. 16, 1999, now abandoned.

(51) Int. Cl.$^7$ ..................... G01N 33/53; G01N 33/559; G01N 33/564
(52) U.S. Cl. ..................... 435/7.1; 435/7.92; 435/7.93; 435/7.94; 435/7.95; 436/507
(58) Field of Search .............................. 435/7.1, 7.92, 435/7.93, 7.94, 7.95; 436/507

(56) References Cited

U.S. PATENT DOCUMENTS

| 5,342,580 A | | 8/1994 | Brenner |
| 5,492,812 A | * | 2/1996 | Vooheis |

FOREIGN PATENT DOCUMENTS

| EP | 0 909 814 | 4/1999 |
| WO | WO 96 20218 | 7/1996 |

OTHER PUBLICATIONS

Foley et al., (1988), "Evidence for the presence of antibodies to cholinergic neurons in the serum of patients with Alzheimer's disease", *Journal of Neurology*, vol. 235, pp. 466–471.
Gaskin, "Human Antibodies to Alzheimer's Disease and Normal Neural Elements", *Antibodies to Alzheimer's Disease*, pp 137–145.
Gaskin et al., (Jan. 1987), "Autoantibodies To Neurofibrillary Tangles and Brain Tissue in Alzheimer's Disease: Establishment of Epstein–Barr Virus–transformed Antibody–producing Cell Lines", *J. Exp. Med.*, vol. 165, pp. 245–250.
Lopez et al., (Aug. 1992), "Serum Autoantibodies in Patients With Alzheimer's Disease and Vascular Dementia and in Nondemented Control Subjects", *Stroke*, vol. 23, No. 8, pp. 1078–1083.

McRae et al., (Aug. 1993), "Cerebrospinal fluid microglial antibodies: potential diagnostic markers for immune mechanisms in Alzheimer's disease", *Behavioural Brain Research*, vol. 57, pp. 225–234.
Mecocci et al, (1993), "Antihistone and Anti–dsDNA Autoantibodies in Alzheimer's Disease and Vascular Dementia", *Society of Biological Psychiatry*, vol. 33, pp. 380–385.
Mecocci et al., (1995), "Serum anti–GFAP and anti–S100 autoantibodies in brain aging, Alzheimer's disease and vascular dementia", *Journal of Neuroimmunology*, vol. 57, pp. 165–170.
Singh et al., (1992), "Immunoblot detection of antibodies to myelin basic protein in Alzheimer's disease patients", *Neuroscience Letters*, vol. 147. pp. 25–28.
Singh et al., (1986), "Detection of Brain Autoantibodies in the serum of patients with Alzheimer's disease but not Down's Syndrome", *Immunology Letters*, vol. 12, pp. 277–280.
Tanaka et al., (1989), "Enzyme–linked immunosorbent assay for human autoantibody to glial fibrillary acidic protein: higher titer of the antibody is detected in serum of patients with Alzheimer's disease", *Acta Neurol. Scand.*, vol. 80, pp. 554–560.
Tchernakov et al., (1992), "Alzheimer's disease and Down's syndrome antibodies bind to the heavy neurofilament protein of cholinergic neurons", *Immunological Factors in Alzheimer's Disease*, pp. 670–675.
Schott et al. (Jan. 31, 1996), "Autoantibody reactivity in serum of patients with Alzheimer' disease and other age related dementia", *Psychiatry Res.*, vol. 50, No. 3, pp. 251–54. (Abstract).
Lopez et al., (Nov. 1991), "Serum auto–antibodies in Alzheimer's disease" *Acta Neural Scand*, vol. 84, No. 5, pp. 441–44. (Abstract).
Ounanian et al., (1990), "Antibodies to viral antigens, xenoantigens and autoantigens in Alzheimer's disease". *J Clin Lab Anal*, vol. 4, No. 5, pp. 367–75. (Abstract).

(List continued on next page.)

*Primary Examiner*—Gary Kunz
*Assistant Examiner*—Stephen Gucker
(74) *Attorney, Agent, or Firm*—McDonnell Boehnen Hulbert & Berghoff LLP

(57) ABSTRACT

The invention relates, among other things, a preparation comprising Alzheimer's disease antigen (A68), as well as methods of obtaining this purified antigen, and methods of using this purified antigen, for instance, for diagnosing Alzheimer's disease and for detecting human autoantibodies to the Alzheimer disease antigen. The antigen preparation according to the invention is purified in that it is substantially free of immunoglobulin G. The invention further relates to methods of making Alzheimer disease antigens that can be used instead of or along with the A68 antigen preparation (e.g., for diagnosing AD), such as recombinant human tau, tau isolated from various species including human, and phosphorylated recombinant human tau or isolated tau, as well as A68 anti-idiotypic antibodies.

5 Claims, 2 Drawing Sheets

OTHER PUBLICATIONS

Loeffler et al, (Feb. 1997), "Immunocytochemical detection of anti–hippocampal antibodies in Alzheimer's disease and normal cerebrospinal fluid", *Neurochem Res.*, vol. 22, No. 2 pp. 209–14. (Abstract).

McRae et al., (May–Aug. 1996), "Microglial Cerebrospinal fluid antibodies. Significance for Alzheimer disease", *Mol. Chem. Neuropathol*, vol. 28, No. 1–3, pp. 89–95. (Abstract).

Dahlstrom et al., (Aug.–Dec. 1994), "Alzheimer's disease cerebrospinal fluid antibodies display selectivity for Microglia. Investigations with cell cultures and human cortical biopsies" *Mol Neurobiol*, vol. 9, No. 1–3, pp. 41–54. (Abstract).

Dahlstrom et al., (1990), "8investigations on auto–antibodies in Alzheimer's and Parkinson's disease, using defined neuronal cultures" *J Neural Transm Suppl.*, vol. 29, 195–206. (Abstract).

Sugiura et al., (Jan. 1989), "Detection of anti–cerebral autoantibodies in schizophrenia and Alzheimer's disease" *J Clin lab Immunol*, vol. 28, No. 1, pp. 1–3. (Abstract).

Bahmanyar et al., (Oct. 1983), "Serum antibodies to neurofilament antigens in patients with neurological and other diseases and in healthy controls", *J. Neuroimmunal*, vol. 5, No. 2, pp. 191–196. (Abstract).

Genovesi et al., (Mar. 1996), "Relationship between autoimmune thyroid disease Rand Alzheimer's disease", *Panminerva Med.*, vol. 38, No. 1, pp. 61–63. (Abstract).

Serot et al., (Sep. 1992), "Antibodies to choroids plexus in senile dementia of Alzheimer's type" *J Clin Pathol*, vol. 45, No. 9, pp. 781–783. (Abstract).

Singh et al., (1989) "Increase of immunoglobin G3 subclass is related to brain autoantibody in Alzheimer's disease but not in Down's syndrome", *Autoimmunity*, vol. 3, No. 2, pp. 95–101. (Abstract).

Kumar et al., (1988) "Serum IgG Brain reactive antibodies in Alzheimer disease and Down syndrome", *Alzheimer Dis. Assoc. Disord*, vol. 2, No. 1, pp. 50–55. (Abstract).

Fransceschi et al., (Jul. 1989), "Neuron–binding antibodies in Alzheimer's Disease and Down's syndrome",*J. Gerontol*, vol., 44, No. 4, pp. 128–30. (Abstract).

Mecocci et al., (Sep. 1992), "Serum autoantibodies against glial fibrillary acidic protein in brain aging and senile dementias" *Brain Behav Immun*, vol. 6, No. 3, pp. 286–92. (Abstract).

Heinonen et al., (Jan. 1993), "Circulating immune complexes in sera from patients with Alzheimer's disease, multi–infaracct dementia and Down's syndrome", *Neurosci Lett*, vol. 149, No. 1, pp. 67–70. (Abstract).

Ryskova et al., (1998), "Serum antibodies against brain tissue in patients with multiple sclerosis", Sb Ved Pr Lek Fak Karlovy University HNradcy Kralove Suppl., vol. 31, No. 4, pp. 407–11. (Abstract).

Henneberg et al., (Nov. 1991), "Antibodies to brain tissue in sera of patients with chronic progressive multiple sclerosis", *J Neuroimmunol*, vol. 34, No. 2–3, pp. 223–27. (Abstract).

Hassin–Baer et al., (Mar. 1992), "Antibodies from Down's syndrome patients bind to the same cholinergin neurofilament protein recognized by Alzheimer's disease antibodies", *Neurology*, vol. 42, No. 3, pp. 551–55. (Abstract).

Vazquez et al., (Aug. 1996), "Antibodies to human brain spectrin in Alzheimer's disease." *J Neuroimmunol*, vol. 68, No. 1–2, pp. 39–144. (Abstract).

Fillit et al., (Mar. 1987, "Antivascular antibodies in the sera of patients with senile demential of the Alzheimer's type", *J Gerontol*, vol. 42, No. 2, pp. 182–184 (Abstract).

David M. Wilson et al., "Free fatty acids stimulate the polymerization of tau and amyloid beta peptides: In vitro evidence for a common effector of pathogenesis in Alzheimer's disease", *American Journal of Pathology*, vol. 150, No. 6, (1997), pp. 2181–2195. XP000952986.

Shi Du Yan et al., "Non–enzymatically glycated tau in Alzheimer's disease induces neuronal oxidant stress resulting in cytokine gene expression and release of amyloid.beta.–peptide", *Nature Medicine*, (1995) 1/7, (693–699). XP002151418.

Mark P. Mattson et al., "4–Hydroxynonenal, a product of lipid peroxidatin, inhibits dephosphorylation of the microtubule–associated protein tau", *Neuroreport*, vol. 8, No. 9–10, 1997, pp. 2275–2281. XP000953016.

Data Base Biosis 'Online! Biosciences Information Service, Philadelphia, PA, US; 1990, Ksiezak–Reding et al., "Mapping of the ALZ 50 Epitope in Microtubule–Associated Proteins Taus", Database accession No. PREV199089120028, XP002151419.

\* cited by examiner

PURIFIED ANTIGEN FOR ALZHEIMER'S DISEASE AND METHODS OF OBTAINING AND USING SAME

This application is a continuation of U.S. patent application Ser. No. 09/334,582, filed Jun. 16, 1999, now abandoned.

A TECHNICAL FIELD OF THE INVENTION

The invention relates to a preparation comprising Alzheimer's disease antigen (A68), to methods of obtaining this purified antigen, and to methods of using this purified antigen preparation, for instance, in diagnosing Alzheimer's disease. The antigen preparation according to the invention is purified in that it is substantially free of immunoglobulin G. The invention further relates to methods of making Alzheimer disease antigens that can be used instead of or along with the A68 antigen preparation (e.g., for diagnosing AD), such as recombinant human tau, tau isolated from various species including human, and phosphorylated recombinant human tau or isolated tau, as well as A68 anti-idiotypic antibodies.

BACKGROUND OF THE INVENTION

Alzheimer's disease (AD) is a progressive neurodegenerative disorder affecting 7% of the population over 65 years of age and characterized clinically by progressive loss of intellectual function and pathologically by a continuing loss of neurons from the cerebral cortex. This pathological impairment usually is correlated with increased numbers of neuritic plaques in the neocortex and with the loss of presynaptic markers of cholinergic neurons. Neuritic plaques are composed of degenerating axons and nerve terminals, as well as possible astrocytic elements, and these plaques often exhibit a central amyloid core.

Another characteristic pathological feature of Alzheimer's disease is development of neurofibrillary tangles. A neurofibrillary tangle is an intraneuronal mass composed of normal intermediate filaments and paired helical filaments having unusual properties, which twist and form tangles. Neurofibrillary tangles are comprised of several different proteins.

Neurochemical studies confirm that neurotransmitter systems are deleteriously affected by Alzheimer's disease. The most consistently and severely affected system is that of the cholinergic neurons located in the Nucleus Basalis of Meynert. In addition, a reduction in somatostatin, substance P, and corticotropin releasing factor are observed.

None of the above-mentioned pathologic states such as neurochemical alterations, neuritic plaques or neurofibrillary tangles are unique to Alzheimer's disease. These impairments also occur in the brains of normal aged individuals and are associated with other diseases such as Guam Parkinson's Disease, Dementia Pugilistica and Progressive Supra-nuclear Palsy. For example, paired helical filaments, the twisted filaments that form the tangles and fill the neurites of plaques, also occur in certain other diseases. In fact, immunologic studies have shown that AD epitopes of paired helical filaments exist in Pick bodies, the spherical structures found in affected neurons in the temporal cortex of brains affected by Pick's Disease. In addition, the densities of neurofibrillary tangles and neuritic plaques within the cerebral cortex of an Alzheimer's disease patient correlates only weakly with the stages of the illness.

Accordingly, the diagnosis of Alzheimer's disease has been extremely difficult. Ante-mortem diagnosis of the disease is performed primarily by exclusion of other diseases. An article entitled, "The Neurochemistry of Alzheimer's Disease and Senile Dementia", by Peter Davies in *Medicinal Research Reviews*, Vol. 3, No. 3, pp. 221–236 (1983), discusses Alzheimer's disease and at page 223 states:

> The problem in the diagnosis of Alzheimer's disease is that there is no positive test: the clinician has to rule out other causes of dementia such as strokes, microvascular disease, brain tumors, thyroid dysfunction, drug reactions, severe depression and a host of other conditions that can cause intellectual deficits in elderly people. Only when all of these problems have been eliminated as a cause of the symptoms should a diagnosis of Alzheimer's disease be accepted.

Post-mortem diagnosis of Alzheimer's disease has been based on determination of the number of neuritic plaques and tangles in brain tissue using specialized staining techniques. However, such diagnostic methods, based on neurohistopathological studies, require extensive staining and microscopic examination of several brain sections. Moreover, the plaques and tangles are not confined to individuals having Alzheimer's disease, but also may occur in the brains of normal, elderly individuals or individuals with other diseases. Thus, a more definitive and reliable method for making the diagnosis is needed.

U.S. Pat. No. 4,666,829 issued to Glenner et al. discloses attempts to identify an antigen specific for Alzheimer's disease. However, the antigen described by Glenner et al. also is present in adults of advanced age who do not have Alzheimer's disease (see Ghanbari et al., *Journal of the American Medical Association*, 263, pp. 2907–2910 (1990)). Therefore, a need still exists for a method of diagnosing Alzheimer's disease as distinct from other diseases or age-related indicia.

Similarly, U.S. Pat. No. 5,492,812 issued to Voorheis et al. describes a diagnostic method for Alzheimer's disease that is carried out by screening for tau peptides in the blood of a patient. This method calls for the use of an antibody or Fab fragment that specifically binds tau peptide derived from either the amino terminal 200 amino acids or carboxy terminal 50 amino acids of a tau protein. This method requires that "the whole of the 200 amino acid N-terminal residues of the various tau proteins as well as some portion of their 50 amino acid most C-terminal residues will be released when cleaved from the filaments by ubiquitin-recognizing proteases or other proteases during degeneration and rupture of the affected neurons" (col. 5, lines 12–19). The method further requires that the cleaved segments find their way into body fluids outside the brain (col. 5, lines 19–22). Accordingly, the method is dependent upon, and is ineffective in the absence of, proteolytic fragmentation of the tau complex of proteins. The method further is dependent upon, and is ineffective in the absence of, the subsequent release of the proteolytic fragments into body fluids. It thus is desirable that a direct means of assay for Alzheimer disease-associated antigens be identified, particularly a means that does not require proteolytic fragmentation and subsequent release into the bloodstream of fragments.

Along these lines, PCT International Application WO 96/20218 of Ghanbari et al. describes the isolation of an antigen associated with Alzheimer's disease and a monoclonal antibody directed against this antigen. This antigen is specific for Alzheimer's disease, being present in high quantities in Alzheimer's Disease patients, and being nearly non-detectable in non-Alzheimer's Disease patients. However, the antigen is described as being only "partially purified" in the preparation of Ghanbari et al., consisting of an aggregate of proteins, with the predominant protein having a molecular weight of about 68,000 daltons, and including tau and hyperphosphorylated tau (see, e.g, Example 2). Accordingly, for some applications, a more purified preparation of this Alzheimer's Disease antigen may be desirable and/or required.

It therefore is an object of this invention to provide, among other things, a purified preparation of an Alzheimer's disease antigen. It is another object of this invention to provide, among other things, a method of diagnosing Alzheimer's disease using the purified preparation. It is a further object of this invention to provide, methods of obtaining the purified preparation of the Alzheimer's disease antigen. These and other objects and advantages of the present invention, as well as additional inventive features, will be apparent from the description of the invention provided herein.

BRIEF SUMMARY OF THE INVENTION

The invention provides, among other things, a preparation comprising Alzheimer's disease antigen (A68), as well as methods of obtaining this purified antigen (Ag), and methods using the purified Ag, for instance, for diagnosing Alzheimer's Disease (AD). This Ag is purified in that it is substantially free of immunoglobulin G (IgG). The invention additionally provides methods of making AD Ags that can be used instead of or along with A68 (e.g., for binding AD autoantibodies), such as recombinant human tau, tau isolated from various species including human, and phosphorylated recombinant human tau or isolated tau, as well as A68 anti-idiotype antibodies (Abs). The invention further describes treatments of these Ags that enhance their reactivity with autoantibodies directed against A68. These treatments include treatment with hypcricin, free fatty acids, and/or hydroxynonenal or other advanced glycation end products.

The invention also describes methods using a bovine microtubule-associated protein preparation (MAPf) for diagnosing AD. The invention describes analysis of autoantibody reactivity with both A68 and MAPf such that either a quantitative or a qualitative analysis of these reactivities provides a diagnosis for AD.

DETAILED DESCRIPTION OF THE PREFERRED EMBODIMENTS

Figure 1:
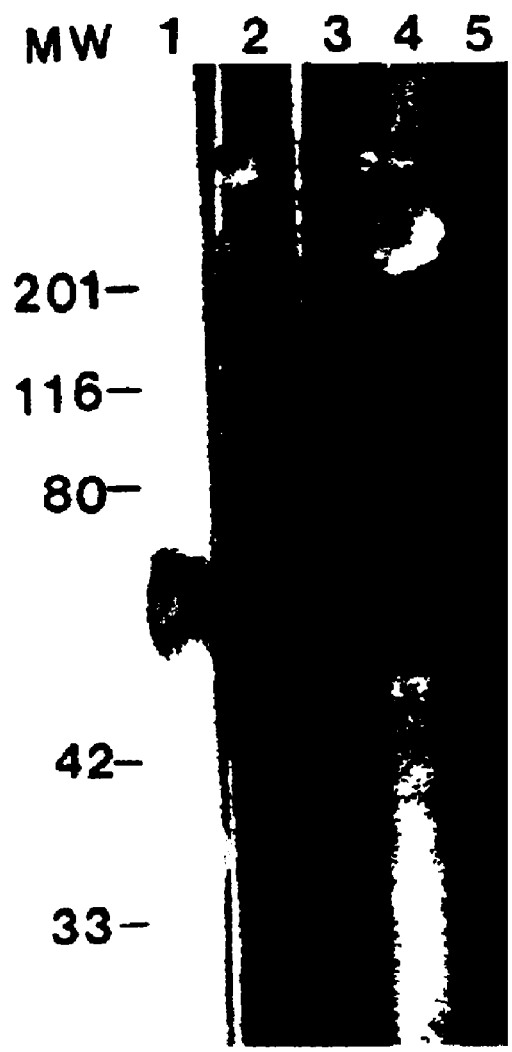
FIG. 1 is a reproduction of a photograph of a Western blot for detection of anti-A68 autoantibodies in Alzheimer's disease patients where the strips were probed with sera from two Alzheimer's disease patients (Patient 1, lane 2; Patient 2, lane 4) and two normal controls (Patient 3, lane 3; Patient 4, lane 5). Relative molecular weights are listed to the left of the blot. Lane 1 demonstrates the A68 banding pattern produced by an anti-A68 monoclonal antibody.

By "individuals with Alzheimer's disease" is meant individuals or patients suffering from, affected by, or manifesting the clinical symptoms of the disease. According to the invention, a diagnosis of "Alzheimer's disease" is based on accepted standards of clinical diagnosis. Preferably, an individual according to the invention diagnosed with Alzheimer's disease is one that has met most (i.e., a majority) of the generally accepted criteria for diagnosis of Alzheimer's disease. Desirably, because of certain atypical features, such an individual may be described by a physician as 'possible Alzheimer's disease', and at least 75% to 85% of these individuals would be found at autopsy to have suffered from Alzheimer's disease. Even more preferably, an individual according to the invention diagnosed with Alzheimer's disease is one that has met the best available clinical criteria: for the diagnosis of Alzheimer's disease, and may be described by a physician as "probable Alzheimer's disease'. When such a diagnosis is made by one skilled in the art, optimally about 90% of these patients would be found on autopsy to have Alzheimer's disease.

Alzheimer's Disease Antigen Preparation

The present invention pertains, inter alia, to the Alzheimer's disease antigen designated A68. The antigen has been described as obtained from the brains and cerebrospinal fluid (CSF) of Alzheimer patients, but is referred to herein as the "Alzheimer antigen" regardless of where it is found in a person if the antigen has the properties set forth herein. It has been discovered that one such Alzheimer antigen is a protein, so that the Alzheimer antigen is also referred to herein as an "Alzheimer protein" when the protein property is a prominent factor in the discussion. The autoantibodies which are immunologically reactive with the Alzheimer antigen are referred to herein as "Alzheimer antibodies." The Alzheimer's disease antigen also refers to components of a preparation containing this antigen that have been modified to increase their reactivity with antibodies directed against the antigen, as further described below.

The identification, isolation, and characterization of the Alzheimer's disease antigen as a "partially purified preparation of A68 antigen" has been described in PCT International Application WO 96/20218 (see, e.g., Example 2 in particular, as well as remainder of this document which is incorporated in its entirety by reference). In particular, PCT International Application WO 96/20218 describes the confinement of this antigen to Alzheimer's disease patients (see, Example 2A, Example 8) as compared to normal individuals, and individuals having other impairments. Generally, the Alzheimer antigen is found in Alzheimer patients while being present in much reduced (or non-measurable) quantities in non-Alzheimer patients, including patients suffering from other neurologic diseases.

The antigen of the invention which is associated with Alzheimer's disease (i.e., the Alzheimer's antigen) is an aggregate of several proteins, and the major protein species have an apparent molecular weight of about 68,000 daltons on a reducing SDS gel. The aggregate migrates electrophoretically as a band or bands on sodium dodecyl sulfate polyacrylamide gel with an apparent $M_r$ of from about 60 to about 70 kDa. A68 desirably is prepared from human brain (typically frozen), most often from cerebral cortex from an Alzheimer's disease patient. Other properties of the A68 antigen are set forth in PCT International application WO 96/20218, and include, but are not limited to, the following characteristics: immunologically reactive with a monoclonal antibody produced by the hybridoma cell line identified as ATCC No. HB9205 (i.e., ALZ-50, further described below); has an isoelectric point of about 6 in reduced or non-reduced form; binds to an affi-Blue column; is at least 50% soluble in a solution of 0.01 M sodium phosphate, 0.14 M sodium chloride and 1 mM phenyl methyl sulfonyl flouride at pH 6.8, and precipitates in 50% saturated ammonium sulfare at 4° C.

Since its first description, the Alzheimer's antigen has been additionally referred to as A68, tau, hyperphosphorylated tau (Lee et al., Science 251: 675–678, 1991), abnormally phosphorylated tau (Grundke-Iqbal et al., Proc. Natl. Acad. Sci. 83: 4913–4917, 1986), soluble PHF (Greenberg and Davies, Proc Natl. Acad. Sci 87: 5827–5831, 1990), PHF tau (Greenberg et al., J. Biol. Chem. 267: 564–569, 1992), and Alzheimer's Disease Associated Protein (ADAP) (Ghanbari et al., JAMA 263: 2907–2910, 1990) All terms are deemed to be equivalent when referring to the Alzheimer's antigen herein. It contains tau and phosphorylated tau. Thus, according to the invention, A68 refers to a form of the microtubule-associated protein tau which, in Alzheimer's disease, is the primary protein constituent of paired helical filaments Relative to normal tau (also a microtubule protein), it is hyperphosphorylated and exhibits an altered conformation.

A68 is obtained in only a "partially purified" form as described in Example 1 of PCT International Application WO 96/20218. By comparison, as described herein, in the process of obtaining a purified preparation of A68 antigen, it was discovered that, not only did the preparation comprise expected elements that needed to be removed (e.g., proteins, etc.), but also, that the preparation surprisingly contained immunoglobulin G (IgG). Removal of such IgG substantially and surprisingly increases the effectiveness of the antigen preparation, and its effectiveness for use in an assay.

Accordingly, the present invention provides a protein preparation consisting essentially of an antigen that is immunologically reactive with a monoclonal antibody produced by the hybridoma cell line identified as ATCC No. HB9205 (i.e., Al2-50), wherein the preparation is substantially free of immunoglobulin G. As used herein, "substantially free of immunoglobulin G" means a preparation having an amount of immunoglobulin G that preferably is equal to or less than about 0.05% of the total protein present in the preparation, and even more preferably is less than or equal to about 0.0015% of the total protein present in the preparation, and/or a total immunoglobulin amount that desirably is less than about 500 pg of immunoglobulin G per µg of A68 (i.e., when A68 amount is assessed by Western analysis with use of the Alz-50 antibody, or by other appropriate means), and optimally is less than about 15 pg of immunoglobulin G per µg of A68. In particular, by substantially free of immunoglobulin G desirably is meant a level of immunoglobulin that does not interfere with the assays of the invention.

Further, the present invention desirably provides a purified preparation of antigen, which preparation is a diagnostic marker of Alzheimer's disease, wherein the antigen preferably comprises a major polypeptide species that:

(a) has an isoelectric point of about 6 in reduced or non-reduced form;

(b) binds to an affi-Blue column;

(c) is at least 50% soluble in a solution of 0.01 M sodium phosphate, 0.14 M sodium chloride and 1 mM phenyl methyl sulfonyl fluoride (PMSF) at pH 6.8, and precipitates in 50% saturated ammonium sulfate at 4° C.;

(d) is immunologically reactive with a monoclonal antibody produced by the hybridoma cell line identified as ATCC No. HB9205 (i.e., Alz-50); and (e) is substantially free of immunoglobulin G (i.e., as described above).

Process for Obtaining an Alzheimer Antigen Protein Preparation

The present invention thus provides a process for obtaining an Alzheimer antigen protein preparation. As a first step, desirably a partially purified preparation is obtained. A partially purified A68 preparation desirably is obtained by a method that comprises:

(a) obtaining a sample of cortical brain tissue containing the antigen;

(b) homogenizing the sample in buffer to obtain a homogenate;

(c) removing particulate matter from the homogenate;

(d) removing the Ag from the homogenate by contacting the homogenate with an antibody (i.e., immobilized AD antibody, as in affinity purification) under conditions wherein the antigen and antibody bind to form an antigen-antibody complex; and (e) eluting the antigen from the antigen-antibody complex to obtain a partially purified protein preparation.

More specifically, this method of preparation desirably is carried out by homogenization of tissue in about 5 volumes of an aqueous buffer such as Tris buffered saline (TBS), preferably where the buffer further contains protease and phosphatase inhibitors. The homogenate optimally is fractionated, e.g., by centrifugation at about 27,000×g for about 60 minutes at about 4° C. Desirably, the supernatant is collected, and passed over an affinity column, preferably in an iterative fashion for about 16 hours at about 4° C. Optimally the affinity column is a MC1 column, desirably which is prepared by using a purified mouse monoclonal antibody (e.g., MC1 antibody, as described in the Examples) which reacts specifically with A68, and coupling the antibody to Affigel-10, according to manufacturer's instructions. Preferably, A68 is specifically removed from the supernatant by attaching to the MC1 column matrix. Following extensive washing with TBS, optimally A68 is eluted from the MC1 column using, for instance, 3 M KSCN. The A68 preparation preferably is subsequently dialyzed against buffer (e.g., TBS) and stored at −80° C. Alternative means of obtaining partially purified A68 preparations are set out, for example, in PCT International Application WO 96/20218.

The preparation obtained by this process is highly enriched in A68, but contains amounts of other proteins. In particular, this preparation contains endogenous human immunoglobulins that comprise approximately from about 1 to about 5% of the total protein. These immunoglobulins interfere with the ability to detect serum autoantibodies to A68 by either Western analysis (e.g., FIG. 2, Examples) or ELISA (e.g., Table 2, Examples). Such an A68 protein preparation is not substantially pure according to the invention, but is only partially purified.

Thus, it is necessary according to the invention to remove the contaminating immunoglobulins prior to analysis of serum autoantibodies, or prior to use of the A68 protein preparation. The invention accordingly provides an additional step (f) in the process described above which step comprises removing immunoglobulin G from the eluent to obtain the antigen preparation that is substantially free of immunoglobulin G. This is accomplished, for instance, by incubation of the A68 preparation, desirably with either Protein A or Protein G, and preferably with both Protein A and Protein G, optimally which have first been immobilized on agarose beads. Desirably, about 1 ml of a partially pure A68 preparation is added to packed Protein A beads (generally about 75 µl) and packed Protein G beads (generally about 75 µl). The sample preferably is placed on a rotator, optimally for about 8 hours at 4° C. After incubation, desirably the beads are spun out of solution, e.g., using a microcentrifuge at about 14,000×g for about 3 minutes. The A68 supernatant preferably then is transferred to a new tube containing packed Protein A and Protein G beads (generally about 75 µl of each) and allowed to incubate, optimally for up to 16 hours on a rotator at 4° C. Subsequently, the Protein A and G beads are pelleted, optionally using a microcentrifuge at about 14,000×g for about 3 minutes. The A68 supernatant is then stored (e.g., in 250 µl aliquots at −80° C.).

Alternately, immunoglobulin G desirably is removed by incubation of the protein preparation with an immunoglobulin G removal method that is substantially equivalent to use of both Protein A and Protein G, such as, for instance, use of fixed bacteria or Pansorbin.

Total protein concentration of the purified A68 antigen preparation desirably is determined by a Coomassie Blue protein assay, for instance, using Coomassie Plus Protein Assay Reagent (Pierce catalog #23236) and the microassay as described by the manufacturer with known concentrations of BSA as a standard. Subsequently, reactivity of the antigen preparation with the A68 specific monoclonal antibody MC15 desirably is determined by chemiluminescent indirect ELISA, and the activity expressed as relative light units (rlu)/ng protein. Protein concentrations of subsequent A68 antigen preparations desirably can be estimated by comparing MC15 reactivity of the subsequent antigen preparations against MC15 reactivity of the initial lot. This method circumvents problems of variability typically encountered when A68 protein concentration is measured using a Coomassie Blue protein assay.

Determination of the immunoglobulin G content of the Protein A/G treated A68 (or the partially purified A68 preparation) desirably can be done by chemiluminescent indirect ELISA using purified human IgG (Sigma, St. Louis, Mo.) as a standard, or by other appropriate means (i.e., particularly means described in the Examples).

Using these methods of the invention, an A68 antigen preparation can be obtained that is substantially free of immunoglobulin G—i.e., which has an amount of immunoglobulin G that preferably is equal to or less than about 0.05% (and even more preferably is equal to or less than about 0.0015%) of the total protein of the preparation, and/or desirably which has less than about 500 pg of immunoglobulin G (and even more preferably has less than about 15 pg of immunoglobulin G) per µg of A68. When the antigen is used for Western blot analysis, the purified A68 preparation preferably contains less than about 500 pg of IgG, and more desirably contain less than about 15 pg IgG per amount of antigen loaded per gel lane. It further is envisioned that substantially immunoglobulin G-free antigen preparations also can be achieved using methods for "blocking" or "typing-up" any IgG present, or other appropriate means of removal of the IgG. Such methods include, but are not limited to: caprylic acid precipitation of A68; adsorption using an anti-human IgG resin; and use of Pansorbin.

Assays Making Use of the Alzheimer's Antigen Protein Preparation

This invention is directed inter alia to the detection of antibodies (autoantibodies) specific for Alzheimer's disease-associated antigen, which antigen is present in individuals with Alzheimer's disease and substantially absent from individuals who do not have Alzheimer's disease. The present invention provides specific and sensitive assays for diagnosis of Alzheimer's disease (i.e., for detecting the presence of autoantibodies to the AD antigen). The methods of the invention overcome the drawbacks of the prior art which require a diagnosis based on a process of elimination of other disorders, and thus provide clarity to an assessment of treatment options.

Thus, this invention desirably is directed to detection of antibodies (i.e., autoantibodies) towards an Alzheimer's disease-associated antigen present in individuals with Alzheimer's disease and substantially absent from individuals who do not have Alzheimer's disease. This invention is also directed to the detection of autoantibodies specific for tau proteins from human, as well as, other species (i.e., desirably a mammalian species), such as bovine tau. Such tau protein antibodies are present in individuals who do not have AD, and are substantially absent from individuals with AD. The present invention provides a specific and sensitive assay for diagnosis of AD. Diagnosis is made based on the relative levels of Alzheimer's antibodies and MAPf autoantibodies present in body fluids, such as serum, plasma, and cerebrospinal fluid, such that individuals with substantial levels of Alzheimer's antibodies, and without substantial levels of autoantibodies to MAPf, are diagnosed as having AD.

This method accordingly provides for the use of Protein A/G treated A68 (i.e., an A68 preparation that is substantially free of immunoglobulin G) as an antigen for detecting autoantibodies which are diagnostic for Alzheimer's disease. It is a novel and unexpected finding of the invention that A68 purified according to the invention to be substantially free of IgG, but not partially purified A68 preparations, can be employed in various methods (e.g., Western blot analysis, chemiluminescent sandwich ELISA assay, chemiluminescent indirect ELISA assay, direct ELISA assay, immunoprecipitation assays, and others) to detect autoantibodies specific for Alzheimer's disease. It will be apparent to one skilled in the art that these assays may be conducted in many ways including direct and/or indirect ELISA, sandwich ELISA, Western blot analysis, etc. Furthermore, it will be apparent that competition assays with any of the various Alzheimer's disease antigens and/or their precursors or related proteins, either alone or in combination, can aid in the detection of autoantibodies diagnostic for Alzheimer's disease.

In these assays according to the invention, desirably, antibodies directed against the Alzheimer disease antigen can be employed. These antibodies include monoclonal antibodies (e.g., as described in PCT International Application WO 96/20218) as well as serum autoantibodies. Certain preferred monoclonal antibodies are described in the Examples which follow. However, one particularly preferred antibody is ALZ-50 secreted by hybridoma No. HB9205, which was deposited under the Budapest Treaty on Sep. 17, 1986 with the American Type Culture Collection, 10801 University Blvd., Manassas, Va. 20110-2209. ALZ-50 has become the standard reagent for detecting the presence of Alzheimer's disease in this field. (See, for example, Wood et al., *Histochemical Journal*, 21, No. 11, pp. 659–662 (1989); Itagaki et al., *Annals of Neurology*, 26, No. 5, pp.685–689 (1989); Beach et al., *Brain Research*, 501, No. 1, pp. 171–175 (1989); Love et al., *Journal of Neuropathology and Experimental Neurology*, 47, No. 4, pp. 393–405 (1988); Nukina et al., *Neuroscience Letters*, 87, No. 3, pp. 240–246 (1988); and Hyman et al., *Brain Research*, 450, pp. 392–397 (1988).)

In the assay methods described herein, the sample used in the assay of the invention is preferably selected from the group consisting of brain tissue, pre or post-mortem, cerebrospinal fluid, urine and blood. In a preferred embodiment, the sample comprises serum. The methods described herein for use with serum are applicable to CSF and urine. The following is another test procedure is believed to be suitable for detecting the presence of autoantibodies to Alzheimer antigen in the blood or other body fluids of a person having Alzheimer's disease. The procedure is similar to the procedure used in the detection of HTLV-III as disclosed in "Immunoassay for the Detection and Quantitation of Infectious Human Retrovirus, Lymphadenopathy-Associated Virus (LAV)", by J. S. McDougal et al., *Journal of Immunological Methods*, 76, pp. 171–183 (1985). Preferably from about 0.1 µl to about 100 µl of serum is utilized, more preferably 0.25 µl to 10 µl of serum is utilized.

Thus, in terms of a Western analysis for detection of autoantibodies that are present in Alzheimer's disease, the present invention provides such a method that optimally comprises:

(a) obtaining an A68 purified protein preparation according to the invention, and a sample being tested for the presence of the autoantibodies;

(b) electrophoresing the protein preparation on a gel;

(c) transferring the electrophoresed protein preparation to a membrane (e.g., nitrocellulose);

(d) contacting the membrane with a sample being tested for the presence of the autoantibodies such that an antigen-autoantibody complex can form; and (e) detecting the autoantibodies by the formation of the complex.

Similarly, in the instant invention, a method is provided for determining the presence of autoantibodies specific to Alzheimer's disease in a sample, thereby diagnosing Alzheimer's disease. The method optionally comprises contacting a sample from an individual suspected of having Alzheimer's disease with a purified A68 antigen preparation according to the invention. In terms of a sandwich ELISA assay (e.g., described in the Examples), this contacting optimally is done after the sample has been allowed to bind to Protein A/G (preferably which has been immobilized on beads, plates, nitrocellulose, fixed bacteria, Pansorbin, and the like). This contacting optionally is done such that the autoantibody is free in solution, and immobilized subsequent to contacting the Ag. Subsequently (e.g., following washing), the mixture desirably is contacted with an antibody specific for an antigenic determinant on the Alzheimer's antigen (e.g., ALZ-50 or monoclonal TG5 specific for A68) and capable of binding so as to produce a complex. According to the invention, the "antibody" can be a portion of an antibody (e.g., a Fab fragment, etc.). The resulting complex then optionally can be separated and recovered from the sample, but preferably, is detected by an appropriate means, e.g. chemiluminescent means, etc.

Optionally, A68 is labeled, as with biotin or radioactive markers by standard protocols, and the complex desirably is measured by detection of that label. This is accomplished, for instance, with reagents such as streptavidin conjugated to horseradish peroxidase in the case of biotin-labeled A68, or through capture of the complex and detection of radioactivity in that complex. Labeling means and means of detecting labels are well known to those skilled in the art.

Accordingly, the invention further provides a method for detecting autoantibodies that are present in Alzheimer's disease comprising:

(a) obtaining a purified A68 protein preparation according to the invention;

(b) contacting the protein preparation with a sample being tested for the presence of the autoantibodies such that an antigen-autoantibody complex can form; and (c) detecting the autoantibodies by the formation of the complex.

As previously described, the method desirably can be carried out where the presence of the autoantibodies is determined by the presence of the complex (i.e., a qualitative test). Optionally, the method can be carried out where the amount of the complex is measured, and the amount of the autoantibodies is determined by the amount of the complex (i.e., a quantitative test).

Additionally, the method optionally can comprise the further step of contacting the complex with an antibody that is immunologically reactive with an antigenic determinant found on either the autoantibody or the protein preparation such that an antigen-antibody or antibody-autoantibody complex is formed.

The antibodies employed in the methods of the present invention optimally can be made detectable by attaching an identifiable label thereto. The antibody preferably is made detectable by attaching to it an enzyme conjugated to an appropriate substrate which, in turn, catalyzes a detectable reaction. The enzyme may be horseradish peroxidase, beta-galactosidase or alkaline phosphatase. Other means of detection of the antibody include attaching a fluorescent, chemiluminescent, or radiolabel thereto. Alternatively, the antibody may be detected by use of another antibody directed to it, the other antibody being labeled or having an enzyme substrate bound to it. The presence of the detectable antibody (e.g., as an indicator of the complex) may be readily detected using well-known techniques. Thus, if the detectable antibody is linked to an enzyme and introduced to an appropriate substrate, the optical density of the detectable bound antibody is determined using a quantum spectrophotometer. If the detectable antibody is fluorescently labeled, the fluorescent emission may be measured or detected using a fluorometer technique. In a similar manner, if the detectable antibody is radioactively labeled, the bound antibody may be detected using radioactivity detection techniques. By comparing the results obtained using the above-described methods on the test sample with those obtained using the methods on a control sample, the presence of the purified A68 protein preparation/autoantibody complex specific to Alzheimer's disease may be determined. The elevated amount of purified A68 protein preparation/autoantibody specific to Alzheimer's disease is thereby detected and may optionally be quantitated.

The methods for qualitatively or quantitatively determining the Alzheimer's disease antigen/autoantibody complex may be used in the diagnosis of Alzheimer's disease. Utilization of the methods of the present invention is advantageous over prior art methods because the present invention provides simple, sensitive, very specific methods for detecting Alzheimers antigen/autoantibody complex. The Alzheimer's antigen is well-suited for sandwich immunoassay complex formation since it is present in aggregate form and, hence, is multiepitopic. This is in contrast to cross-reactive proteins, which are soluble and usually contain one epitope per protein.

Variations of these and other standard methods for detection of autoantibodies and autoantigens would be evident to one skilled in the art, and are contemplated by the invention.

Method of Making Alzheimer Disease Antigens for Detecting Autoantibodies

The invention also desirably provides a method of increasing the ability of an Alzheimer's disease antigen to detect autoantibodies that are present in Alzheimer's disease, wherein the antigen is tau isolated from various species including human, or is recombinant human tau. The resulting antigen preparation optionally can be employed instead of (or in addition to) the substantially pure A68 preparation of the invention.

One such method comprises phosphorylating the antigen. Preferably the phosphorylation is done using a cell extract prepared from a central nervous system (CNS) cell line, e.g. neuroblastoma cells (especially MSN neuroblastoma cells), optionally which has been treated with a phosphatase inhibitor, such as okadaic acid. Also, desirably the phosphorylation is done using a purified or partially purified kinase which has been associated in the literature with tau phosphorylation. Such kinases which can be used in the context of the invention include, but are not limited to, PKA, GSK, cdc2, cdc25, casein kinase I and II, MAP kinase, and PHF kinase.

The invention further provides a method of increasing the ability of an Alzheimer's disease antigen to detect autoantibodies that are present in Alzheimer's disease, preferably wherein the antigen is tau isolated from various species including human, or is recombinant human tau, or phosphorylated recombinant human tau (Ptau) or phosphorylated isolated tau, and the method comprises optionally treating the antigen with hypericin.

Similarly, the invention desirably provides a method of increasing the ability of an Alzheimer's disease antigen to detect autoantibodies that are present in Alzheimer's disease, wherein the antigen is tau isolated from various species including human, or is recombinant human tau (rht), or is phosphorylated recombinant human tau (phospho-rht) or phosphorylated isolated tau, and the method comprises treating the antigen with free fatty acids. Preferably the fatty acids are unsaturated fatty acids, particularly oleic or linoleic acids, and most preferably arachidonic acid.

Moreover, the invention also provides a method of increasing the ability of an Alzheimer's disease antigen to detect autoantibodies that are present in Alzheimer's disease, wherein the antigen is tau isolated from various species including human, or is recombinant human tau, or phosphorylated is recombinant tau (phospho-rht) or phosphorylated isolated tau, and the method optionally comprises treating the antigen with advanced glycation endproducts, especially where the advanced glycation endproduct is the lipid peroxidation product 4-hydroxy-2-nonenal (HNE).

Anti-Idiotypic Antibodies

The invention further provides a means of obtaining so-called "anti-idiotypic antibodies", which are antibodies that recognize amino acid differences in, and hence are specifically directed to, particular immunoglobulins. In particular, the invention preferably provides means of identifying anti-idiotypic antibodies to A68 Alzheimer's disease antigen-reactive immunoglobulins, starting from either monoclonal antibodies to A68 or human serum autoantibodies to A68. These anti-idiotypic antibodies desirably are employed in the methods of the invention for assaying for Alzheimer's disease.

Accordingly, the invention desirably provides an antibody (e.g., especially a monoclonal antibody) that is immunologically reactive with an antibody (e.g., especially a monoclonal antibody, or human serum autoantibody) directed against A68 antigen. Such an anti-idiotypic antibody, especially an antibody that is immunologically reactive with a monoclonal antibody or human serum autoantibody directed against A68 antigen, desirably is obtained by:

(a) obtaining sera from individuals having high titers of anti-A68 autoantibodies, combining to create a pool, and isolating antibodies from said pool, or, obtaining isolated monoclonal antibodies to A68 antigen;

(b) immunizing mice with the isolated antibodies;

(c) obtaining serum from the mice (i.e., after sufficient time and under sufficient conditions for antibodies to be produced); and (d) testing the serum to identify mice having high levels of antibodies that are immunologically reactive with an antibody (e.g., a monoclonal antibody or human serum autoantibody) directed against A68 antigen.

The method optionally can be carried out comprising the further steps:

(a) obtaining the spleens of the mice having high levels of antibodies that are immunologically reactive with a monoclonal antibody or human serum autoantibody directed against A68 antigen;

(b) fusing the spleens with myeloma cells and plating onto tissue culture plates;

(c) selecting for fused cells by HAT resistance; and (d) testing said fused cells for production of antibodies that are immunologically reactive with an antibody (e.g., a monoclonal antibody or human serum autoantibody) directed against A68 antigen. Optimally the method further comprises testing the fused cells for production of antibodies that are not immunologically reactive with antibodies not directed against A68 antigen. Suitable variations of these methods will be apparent to those skilled in the art.

Bovine Tau (MAPf) Preparation and Assays

This invention further desirably provides for the use of a bovine microtubule-associated protein preparation (i.e., MAPf) in conjunction with A68, for instance, in Western blot analysis of sera. Bovine MAPf contains, among other things, 70% MAPs 1 & 2, 20% other MAPs, and 10% Tau MAP isoforms. The current invention, as described herein, makes use of the six Tau MAP isoforms that migrate in the 40–65 kD range on a 10% SDS polyacrylamide gel. The methods for electrophoresis, Western transfer, sera incubation, and detection of bound autoantibody are well known to those skilled in the art.

Thus, desirably according to the invention, an individual can employ for electrophoresis alternating lanes of A68 and MAPf. MAPf preferably is used at the concentration of 1.5 ug total protein/lane. Following electrophoresis, the protein is transferred to an appropriate support, e.g., nitrocellulose, or other membrane. Desirably, patient sera is incubated with the strips of nitrocellulose containing purified A68 protein preparation and strips of nitrocellulose containing MAPf; and bound autoantibodies are then visualized as previously described. Under these conditions, bound autoantibodies to purified A68 protein preparation and the tau isoforms in MAPf desirably are obtained.

Accordingly, the present invention also desirably provides a method for detecting autoantibodies that are present in Alzheimer's disease comprising the steps of:

(a) obtaining a purified A68 protein preparation as previously described, a bovine microtubule associated protein preparation, and a sample being tested for the presence of autoantibodies;

(b) electrophoresing the A68 protein preparation and the bovine microtubule associated protein preparation on separate lanes on a gel;

(c) transferring the electrophoresed A68 protein preparation and the bovine microtubule associated protein preparation to a membrane;

(d) contacting the membrane with a sample being tested for the presence of said autoantibodies such that an autoantibody complex can form with antigen present in the A68 protein preparation and/or with antigen present in the bovine microtubule associated protein preparation; and (e) detecting the autoantibodies by the formation of the complex(es).

Two methods of analysis preferably are used to assign a diagnosis to each serum tested. In the first method, the total optical density (OD)×mm signal from purified A68 protein preparation is divided by the total OD×mm signal from the tau isoforms. In general, the sample is assigned the diagnosis of AD, or non-AD on the basis of this ratio. Optical density can be calculated, for instance, as described in Example 11.

The second method optimally takes into account not only optical density measurements, but also the number of MAPf tau isoforms identified by a given serum. In this method of analysis, if a bovine MAPf tau signal is present in conjunction with purified A68 protein preparation, desirably the sample is assigned a diagnosis of AD if the tau signal contains less than three isoforms, and a diagnosis of non-AD if the sample identifies 3 or more isoforms of tau. In addition, preferably the sample is classified as non-AD if it lacks purified A68 protein preparation signal, regardless of the number of tau bands. Quantification of the MAPf tau signal in this instance takes on the formula: (Sum OD×(n−2)). For this formula, "Sum OD" is the sum of OD×mm measurements of all tau isoforms and "n" is the total number of bands present of the six tau MAPf isoforms. Thus, samples that give a purified A68 protein preparation signal and lack a substantial tau signal by this method are termed AD, and all other combinations (A68 signal+tau signal, tau signal alone, or absence of both signals) are diagnosed as non-AD.

Preferably the use of tau isoforms is not limited to use of bovine tau isoforms found in MAPf. Other forms of tau protein desirably are used, including but not limited to, tau purified from brain, and recombinant tau, either as a single molecule or as a mixture of tau isoforms. Additionally, the invention is not limited to tau from a bovine species. Purified tau or MAP from brains or cultured cells of other species may be used such as human, rodent, or other mammalian sources, as well as preparations from avian and reptiles.

Similarly, autoantibodies reactive with purified A68 protein preparation and bovine tau may also be detected in an indirect ELISA assay wherein the antigen is immobilized in a microtiter plate in which the bottom of each well is nitrocellulose. This support allows the antigen to be displayed in a manner which more closely resembles the Western blot than does a polystyrene support. Millipore MHAB plates are prewet with BBS for 1 minute, then the buffer is drawn through the filter under vacuum. Antigen is applied to the wells in BBS at 0.01 to 10 µl per well (0.3 to 300 ng), and allowed to bind for 3 hours at 24° C. In these experiments, the antigen may be purified A68 protein preparation, bovine tau (MAPf), or purified A68 protein preparation analogues such as phosphorylated rht. The antigen solution is drawn through the filter under vacuum, and the filters are blocked with 5% non-fat dry milk in BBS for 1.5 hr at 24° C. Subsequently, all incubation solutions are removed by plate washer (Nunc) and washed with 0.1% tween 20 in tbs (defined earlier) rather than by drawing through the membrane under vacuum. 1% serum is added to wells in 100 µl of 1% non-fat dry milk, 5% normal goat serum, BBS, and incubated for 16 hr at 4° C. Bound human Ig is detected by addition of HRP-conjugated goat anti-human Ig in 1% casein/tbs for 2 hr at 24° C. followed by addition of 90 µl LumiGlo (Kirkegaard and Perry) chemiluminescent substrate. Chemiluminescence is measured as described in Example 5.

EXAMPLES

The invention is illustrated further by the following examples which are not to be construed as limiting the invention in scope or spirit to the specific compounds or procedures described in them, or as in any other way limiting the invention's scope.

Example 1
Isolation of a Partially Purified A68 Antigen Preparation

This Example describes the isolation of a partially purified A68 antigen preparation.

A68 antigen was isolated from frozen human brain samples (typically the cerebral cortex from an Alzheimer's disease patient), by homogenization in 5 volumes of an aqueous buffer such as tris buffered saline (TBS), containing standard protease and phosphatase inhibitors. The homogenate was fractionated by centrifugation at 27,000×g for 60 minutes at 4° C., and the supernatant was collected and passed over an MC1 affinity column iteratively for 16 hours at 4° C. The MC1 column was prepared by coupling a purified mouse monoclonal antibody which reacts specifically with A69 (MC1, described in PCT International Application WO 96/20218, and deposited in terms of its source, secreting hybridoma ATCC No. 11736, with the American Type Culture Collection, Rockville, Md. on Oct. 26, 1994) to Affigel-10 (Biorad Laboratories) according to manufacturer's instructions. A68 is specifically removed from the supernatant by the MC1 column matrix. Following extensive washing with TBS, A68 was eluted from the MC1 column using 3 M KSCN. It subsequently was dialyzed against TBS and stored at −80° C. Other means of isolating a partially purified A68 antigen preparation (which in some instances are similar, if not identical, to that above) are described in PCT International Application WO 96/20218.

The obtained preparation is highly enriched in A68, but also contains amounts of other proteins. The quantity of human Ig in A68 was ascertained through indirect ELISA wherein A68 is coated onto an ELISA plate and probed with horseradish peroxidase (HRP)-conjugated goat antibodies reactive specifically with human Ig. Standard amounts of purified human Ig are coated in other wells and used as standards. Bound HRP-conjugated Abs are quantitated using chemiluminescent HRP substrates, and the quantities between the standard human Ig and the A68 preparations are compared. Surprisingly, the A68-enriched preparation was found to contain endogenous human immunoglobulins comprising approximately 1–5% of the total protein. This is surprising since such immunoglobulins would be expected to be removed during affinity chromatography. As confirmed by the Examples below, this unexpectedly high level of immunoglobulin interferes with the ability of the preparation to detect serum autoantibodies to A68 by either Western blotting or ELISA.

Example 2
Protein A/G Treatment of A68 Preparations

This Example describes the further purification with use of protein A/G of an A68 antigen preparation obtained, for instance, as described in Example 1. Unless otherwise specified, all chemicals for this study, and those in the following Examples, were purchased from Sigma (St Louis, Mo.).

To remove the contaminating Ig's prior to analysis of serum autoantibodies, the A68 preparation was incubated with both Protein A and Protein G immobilized on agarose beads (Immunopure Immobilized Protein A, Immunopure Immobilized Protein G; Pierce, Rockford, Ill.). Briefly, 1 ml of A68 was added to 75 µl of packed Protein A beads and 75 µl of packed Protein G beads. The sample was placed on a rotator for 8 hours at 4° C. After incubation, the beads were spun out of solution in a microcentrifuge at 14,000×g for 3 minutes. The A68 supernatant was then transferred to a new tube containing 75 µl each of packed Protein A and Protein G beads and allowed to incubate for an additional 16 hours on a rotator at 4° C. Subsequently, the Protein A and G beads were pelleted using a microcentrifuge at 14,000×g for 3 minutes, and the A68 supernatant was then stored in 250 μl aliquots at −80° C. Determination of IgG content of the Protein A/G treated A68 was done by chemiluminescent indirect ELISA using purified human IgG (Sigma, St. Louis, Mo.) as a standard as described in Example 1. The preparation was found to be essentially free of endogenous IgGs, having an amount of IgG equal to or less than 0.05% of the total protein of the sample.

Example 3

Western Blot Analysis

This Example describes Western blot analysis of an A68 antigen preparation that has been purified to be substantially free of immunoglobulin by treatment with Protein A/G, as described in the preceding Example.

Gel electrophoresis was performed using the method of Laemmli (*Nature,* 227 pp. 680–685 (1970)), employing 10% SDS-polyacrylamide minigels of about 1.5 mm thickness. Protein A/G treated A68 was loaded at about 100–1000 ng total protein/lane in sample buffer.

Western transfer was performed according to the method of Towbin et al. (*Proc. Natl. Acad. Sci. USA,* 76, pp. 4350–4354, (1979)) using either 0.45 μm or 0.2 μm nitrocellulose (Micron Separations Inc. Westboro, Mass.). Following transfer, the nitrocellulose blots were removed and put into blocking buffer consisting of 5% nonfat dry milk in borate buffered saline (BBS, 75 mM NaCl, 100 mM $H_3BO_3$, 25 mM $B_4Na_2O_7$:10 $H_2O$) for about 2 hours at room temperature. The nitrocellulose was then cut to separate the individual lanes of protein. The strips of nitrocellulose were incubated on a rocker with patient serum at dilutions of 1:100 to 1:1200, for about 16 hours at 4° C. in 1% nonfat dry milk in BBS+5% normal goat serum. Subsequently, the strips were washed twice, 5 minutes each wash, with BPS+ 0.05% Tween-20, followed by a final 45 minute wash with BBS+Tween-20. Washes were performed at ambient temperature on a shaker.

Goat-anti-human IgG-HRP antibody (Southern Biotechnology Associates, Birmingham, Ala., Cat #2040-05) was then added to the strips at about 0.1 μg/ml in 1% nonfat dry milk in BBS and the strips were incubated for about 1.5 hours on a shaker at ambient temperature. The nitrocellulose strips were then washed 4 times, 5 minutes each, with BBS+0.05% Tween-20. The strips were then soaked for 5 minutes in ECL (LumiGLO, Kirkegaard and Perry, Gaithersburg, Mass., Cat. #50-59-00). The excess LumiGLO was allowed to drain from the strips, which were then placed in a plastic page holder. The strips were then overlaid with preflashed X-ray film (Hyperfilm, Amersham, Arlington Heights, Ill.) for 1–30 min. Preflash of the X-ray film was carried out using the Amersham Sensitize unit as prescribed by the manufacturer. The X-ray film was then developed by standard methods to visualize the A68 signal.

In terms of positive and negative controls for the Western analysis, sera were run at several dilutions ranging from 1:100 to 1:1200. The sera were incubated with nitrocellulose strips (i.e., corresponding to gel lanes) that contained protein A/G-treated A68 in sample buffer, or sample buffer alone. Additionally, a lane of protein A/G A68 was processed as described, with the exception that human sera was left out in the first incubation step (i.e., the lane was probed with goat-antihuman IgG-HRP antibody only). Both of these measures serve as negative controls. As a positive control, one lane of A68 was probed with a monoclonal antibody to A68, such as Alz50 or TG5 (i.e., PCT International Application WO 96/20218, and TG5 is further discussed below). Sera were scored as positive if they exhibited positive staining of A68 bands in the ~60–70 kD range on the Western blot, but otherwise, were negative in the lanes that contained sample buffer only. Sera were scored as negative if they lacked visible bands in the ~60–70 kD range.

Figure 2:
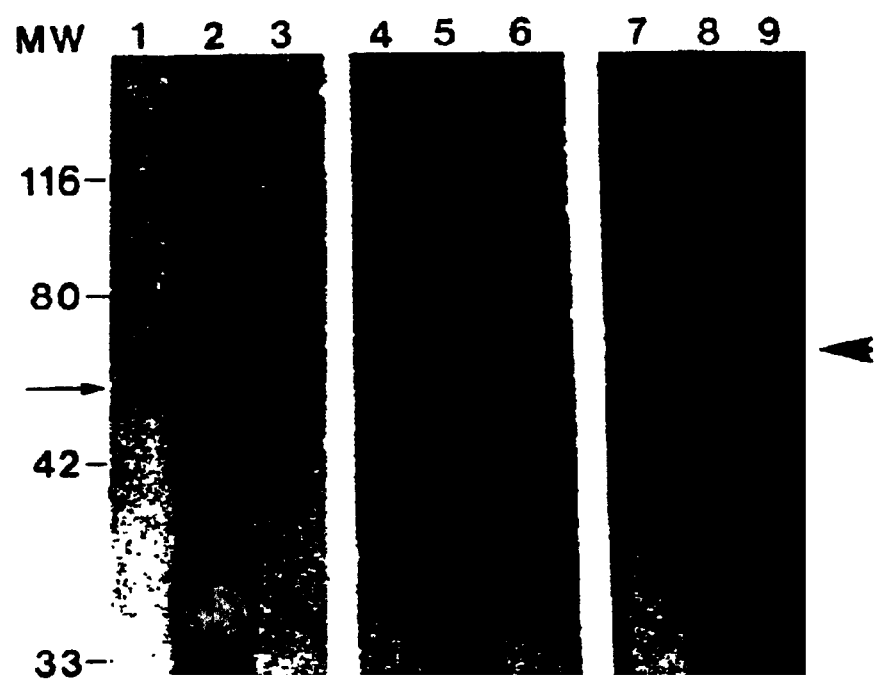
FIG. 2 is a reproduction of a photograph of a Western blot for detection of anti-A68 autoantibodies in Alzheimer's disease patients using two lots of partially purified A68 preparation ("Lot A", lanes 1–3, and "Lot B", lanes 4–6) and one lot of Protein A/G treated A68 preparation (lanes 7–9). The strips were probed with sera from two Alzheimer's disease patients (Patient 1, lanes 2, 5, 8 or Patient 2, lanes 3, 6, 9) followed by goat anti-human IgG-HRP, or the strips were probed for IgG endogenous to the A68 preparations using the goat anti-human HRP antibody only (lanes 1, 4, 7). Symbols: Arrow, ~55 kD, shows the heavy chain of IgG; Arrowhead, shows the prominent A68 bands.

Results of these studies are set out in FIGS. 1 and 2. As can be seen from FIG. 1, autoantibodies to A68 were present in individuals with Alzheimer's disease (lanes 2 and 4), while normal controls lacked reactivity with the A68 protein (lanes 3 and 5).

Next, the necessity of protein A/G treatment of the A68 preparation for the detection of serum autoantibodies in Alzheimer's disease by Western blotting was ascertained, and is presented in FIG. 2. Two lots of untreated A68 prepared as described in Example 1 (Lot A, lanes 1–3 and Lot B, lanes 4–6) and one lot of Protein A/G treated A68 as described in Example 2 (lanes 7–9) were run on a 10% SDS polyacrylamide gel and transferred to nitrocellulose. Total protein loaded was approximately 175 ng/lane. The strips were probed with sera from two Alzheimer's disease patients (Patient 1, lanes 2, 5, 8 or Patient 2, lanes 3, 6, 9) followed by goat anti-human IgG-HRP, or the strips were probed for IgG endogenous to the A68 preparations using the goat anti-human IgG HRP antibody only (lanes 1, 4, 7). Blotting of untreated A68 shows the presence of a 55 kD band representing the heavy chain of IgG (indicated by the arrow in FIG. 2). Furthermore, the untreated A68 reacted weakly or not at all with autoantibodies in human sera Protein A/G treated A68 lacked endogenous IgG reactivity but was recognized strongly by serum autoantibodies to A68 as evidenced by the prominent A68 bands (indicated by the arrowhead in FIG. 2). Protein A/G treatment not only eliminated endogenous IgGs but also enriched for A68 resulting in enhanced autoantibody reactivity.

This Example confirms that Western blot assays using an A68 antigen preparation that has been purified to be substantially free of immunoglobulin by treatment with Protein A/G (as described in Example 2), but not A68 antigen preparation that have not been subjected to this additional level of purification, can be employed to detect Alzheimer's disease autoantibodies.

Example 4

Chemiluminescent Sandwich ELISA Assay

T1 is example describes a chemiluminescent sandwich ELISA assay for the detection of autoantibodies to A68.

For these studies, Dynex microtiter plates type Microlite 1 were coated with 5 μg/ml Pierce Protein A/G for 3 hours at 24° C. in 25 mM $NaPO_4$, pH 7.2, 125 mM NaCl, 2 mM EDTA, 2 mM $NaN_3$, (coat buffer) and were subsequently blocked with a diluent (Casein/TBS) consisting of 1% casein, 10 mM Tris-Cl, pH 7.4, 140 mM NaCl, and 1 mM $NaN_3$ for 1 hour at 24° C. Human serum or plasma, collected and prepared according to standard practices, was incubated in the wells as a 1% solution in Casein/TBS, and allowed to bind for about 3 hours at 24° C. Protein A/G purified A68 was then added at 70 ng/ml in Casein/TBS, and incubated in the wells for 90 hours at 4° C.

TG5, a mouse monoclonal IgG which is highly selective for A68 (described in PCT International Application WO 96/20218, and deposited in terms of its source, secreting hybridoma ATCC No. HB 11746, with the American Type Culture Collection, Rockville, Md. on Oct. 26, 1994), was processed to produce a F(ab')$_2$ fragment conjugated with horseradish peroxidase (HRP, see below). This conjugate was incubated in the wells of the same plates that were pretreated with human serum or plasma at 0.25 μg/ml for 3 hours at 24° C. in Casein/TBS, to react with the A68 that had been captured by autoantibodies. Bound TG5-HRP was then detected using a luminol-based chemiluminescent substrate (i.e., Lumiglo, Kirkegaard and Perry). Luminescence was quantitated with a Labsystems luminometer at high gain using a 5 sec/well read time. All incubations were 100 µl except for the blocking step, which was 288 µl, and the luminol, which was 88 µl. In between each step, the microtiter wells were washed 5 times with a solution of 0.1% Tween 20 in 10 mM Tris-Cl, pH 7.4, 140 mM NaCl, 1 mM NaN$_3$ (TBS) to remove unbound materials.

TG5 was prepared for these studies as follows. TG5 was purified from tissue culture supernatants on immobilized Protein A. It was dialyzed into 50 mM NaPO$_4$, pH 8.1, at a concentration of greater than 5 mg/ml. It was digested to a F(ab')$_2$ with immobilized ficin according to manufacturer's instructions (Pierce). The F(ab')$_2$ fragment was removed from the Fc fragment and residual intact IgG by passing the digest over a Protein A column. To generate a Fab', TG5 was dialyzed against 0.1 M NaPO$_4$, pH 6.0, 5 mM EDTA and reduced with 6 mg/ml mercapto-ethylamine for 90 minutes at 37° C. The buffer was changed to 0.1 M NaPO$_4$, pH 7.0, 5 mM EDTA by desalting on a Sephadex G25 column, and the Fab' containing fractions were pooled and concentrated to greater than or equal to 1 mg/ml. Pierce maleimide-HRP, at a mass ratio of 1:2, TG5:HRP, was added and allowed to react for 1 hour at 24° C., then an additional 16 hours at 4° C. The resulting conjugate was used without further processing.

Three serum samples obtained from patients which were clinically diagnosed as having Alzheimer's disease according to NINCDS-ADRDA criteria were analyzed using the above protocol. Results of these studies are shown in Table 1.

TABLE 1

Autoantibody Detection in Clinical Specimens

| Sample # | Clinical Diagnosis | Relative Light Units, blank subtracted |
| --- | --- | --- |
| DT | AD | 9.01 |
| 836 | AD | 2.04 |
| 5114 | AD | 1.21 |

For each of the three samples, autoantibodies were detected as can be seen from the signal expressed in relative light units in Table 1.

This Example confirms that a chemiluminescent sandwich ELISA assay using an A68 antigen preparation can be employed to detect Alzheimer's disease autoantibodies.

Example 5
Chemiluminescent Indirect ELISA

This example describes a chemiluminescent indirect ELISA assay for the detection of autoantibodies to A68.

For these studies, Protein A/G-treated A68 was added to bicarbonate coating buffer (35 mM NaHCO$_3$, 15 mM Na$_2$CO$_3$, pH 9.65, 0.2 µm sterile filtered) at a concentration of 1 µg/ml, and 100 ul/well was added to a MICROLITE 2 microtiter plate (Dynex Technologies, Chantilly, Va.). The A68 was allowed to adsorb to the wells for 2 hours at 25° C., or 16 hours at 4° C. For determination of background, corresponding wells were coated with bicarbonate buffer only. The wells are then washed 3 times with wash buffer (10 mM Tris(hydroxymethyl)-aminomethane, 150 mM NaCl, 0.1% Tween-20, pH 7.4) using a 12 well washer (Immuno Wash 12, Nunc, Denmark). Subsequently, the wells were blocked for 2 hours at 25° C. with 300 µl/well of 1% Casein/TBS (1% casein (sodium salt), 25 mM Tris (hydroxymethyl)-aminomethane, 145 mM NaCl, 0.01% thimerisal, pH 7.5, sonicated for 6 hours at 10 watts with a Vibro Cell Sonicator at 25° C. (Sonics Materials, Danbury, Conn.), and then filtered through a 0.45 µm SFCA membrane). The wells were then washed 3 times with wash buffer.

Serum diluted 1:500–1:1000 in 1% Casein/TBS with 5% normal goat serum was added to the wells (100 µl/well) and incubated at 25° C. for 2 hours. The wells were then washed 8 times with wash buffer. Subsequently, 100 µl of 0.1 µg/ml goat antihuman IgG-HRP (Southern Biotechnology Associates, Birmingham, Ala.) in 1% Casein/TBS was added to the wells and allowed to incubate for 1.5 hours at 25° C. Following this incubation, the wells were washed an additional 8 times with wash buffer. 88 µl of ECL (LumiGLO, Kirkegaard and Perry, Gaithersburg, Mass.) was added to the wells and the wells were counted for 2 seconds each at 21° C., integral mode, using a Lumionskan RS luminometer (Labsystems, Finland). Unless otherwise specified, all chemicals were purchased from Sigma (St. Louis, Mo.).

To determine the absolute value for a serum sample the relative light unit (RLU) signal from sera in the bicarbonate buffer-only wells was subtracted from the RLU signal from sera in the A68-coated wells. Plate-to-plate and day-to-day variations were corrected for by using an A68 standard curve ranging from 25 ng/well with doubling dilutions to 0.1 ng/well. Detection of the A68 in the standard curve was accomplished by using the A68-specific monoclonal antibody MC15 (1 µg/ml, described in PCT International Application WO 96/20218, and deposited in terms of its source, secreting hybridoma ATCC No. HB 11739, with the American Type Culture Collection, Rockville, Md. on Oct. 26, 1994) and a secondary goat anti-mouse IgM-HRP (0.1 µg/ml, Southern Biotechnology Associates), both diluted in 1% Casein/TBS.

Results of this assay are depicted in Table 2.

TABLE 2

Indirect ELISA for autoantibody detection

| Sample # | Clinical Diagnosis | Relative Light Units (background substracted) |
| --- | --- | --- |
| 5186 | AD | 898.8 |
| 8131 | AD | 432.9 |
| 5178 | AD | 267.1 |
| 5188 | AD | 150.5 |
| 6010 | AD | 95.8 |

As can be seen from Table 2, autoantibodies were detected by the indirect ELISA in all five AD patients, as confirmed by the signal expressed as relative light units.

This Example confirms that a chemiluminescent indirect ELISA assay using an A68 antigen preparation purified according to the invention can be employed to detect Alzheimer's disease autoantibodies.

Example 6
Detection of Autoantibodies in AD

This example describes the production and use of anti-idiotypic antibodies for the detection of autoantibodies in Alzheimer's disease.

Monoclonal antibodies to A68 and/or human serum autoantibodies to A68 are used to produce monoclonal anti-idiotypic antibodies. The anti-idiotypic antibodies are then used as the antigen in an indirect ELISA to screen for anti-A68 autoantibodies in serum from individuals suspected of having Alzheimer's disease. Such use of anti-idiotypic antibodies forms the basis for a serum test for Alzheimer's disease.

Human sera from individuals with Alzheimer's disease are screened by Western blotting against A68. Sera from individuals that are shown to have high titers of anti-A68 autoantibodies are pooled. Human antibodies are isolated from the pooled serum by batch incubation with Protein A/G immobilized on agarose beads. Alternatively, immunoaffinity columns using A68 can be used to enrich for A68 autoantibodies which are subsequently eluted off of the column. The eluted antibodies are then captured as above, using Protein A/G beads. Typically, 1 ml of Protein A/G binds 6–8 mg of IgG. For isolation of human IgG from sera, the sera is diluted 1:1 with 10 mM Tris, pH 7.5 and incubated for 2 hours at 4° C. with 1 ml of Protein A/G beads. For immunoaffinity purified A68 autoantibodies, or monoclonal antibodies in tissue culture soup, the Protein A/G beads are added directly to the antibody solution at a concentration that is proportional to IgG content (i.e., about 1 ml of Protein A/G beads per 6–8 mg of IgG).

Anti-idiotypic monoclonal antibodies are produced using standard methods (see Harlow, E. and Lane, D., Antibodies: A Laboratory Manual, *Cold Spring Harbor Laboratory Press*, (1988)). Briefly, Balb/c mice are immunized by intraperitoneal injections consisting of 10–15 µl of Protein A/G beads loaded with anti-A68 autoantibodies from sera as described above (A/G A68 antibody/bead) in Freund's complete adjuvant. Subsequent boosts occur on days 14 and 21 with Protein A/G beads loaded with anti-A68 autoantibodies (A/G-A68-Ab-beads) in Freund's incomplete adjuvant. On day 31, the mice are tail bled and the serum is tested for the presence of anti-idiotypic antibodies by competition ELISA using A68 (described below). Spleens of mice displaying high titers of anti-idiotypic antibodies are fused with SP2/O-Ag8 myeloma cells and plated into 96 well tissue culture plates. Fused cells are selected for by HAT resistance and the resulting clonal populations are screened by indirect ELISA for the presence of anti-idiotypic antibodies to A68 autoantibodies. Clonal populations that test positive for anti-idiotypic antibodies are further subcloned by standard techniques to produce monoclonal hybridoma populations.

Initial and subsequent clones for anti-idiotypic antibodies to A68 autoantibodies are identified using an indirect ELISA. The following protocol is used to identify anti-idiotypic antibodies raised against autoantibodies to A68: 96 well ELISA plates are coated with 100 µl/well of 1 µg/ml goat anti-mouse IgG Fc specific antibodies in bicarbonate buffer (35 mM $NaHCO_3$, 15 mM $Na_2CO_3$, pH 9.65, 0.2 µm sterile filtered) for 2 hours at 25° C. The wells are washed 3 times with wash buffer (10 mM Tris(hydroxymethyl)-aminomethane, 150 mM NaCl, 0.1% Tween-20, pH 7.4) and subsequently blocked for 2 hours at 25° C. with 300 µl/well of 1% Casein/TBS.

The wells are washed 3 times with wash buffer. Tissue culture media from the hybridoma wells to be tested is then added to the microtiter plate at a dilution of 1:100 in 1% Casein/TBS and allowed to incubate for 2 hours at 25° C. The wells are washed 3 times with wash buffer and then pooled human sera from Alzheimer's disease patients that were used as the original immunogen is added to the wells at a dilution of 1:100 in 1% Casein/TBS. After a 2 hour incubation at 25° C., the wells are washed 8 times with a wash buffer. Subsequently, 100 µl of 0.1 µg/ml goat anti-human IgG-HRP (Southern Biotechnology Associates, Birmingham, Ala.) in 1% Casein/TBS is added to the wells and allowed to incubate for 1.5 hours at 25° C. Following this incubation, the wells are washed an additional 8 times with wash buffer. 88 µl of ECL (LumiGLO, Kirkegaard and Perry, Gaithersburg, Mass.) is added to the wells and the relative light units (RLU) are recorded by counting the individual wells for 1 sec each at 21° C., integral mode, using a Lumionskan RS luminometer (Labsystems, Finland).

A duplicate plate is set up in parallel and treated the same way except in this case the sera is derived from normal individuals that lack autoantibodies to A68. Positive clones containing only anti-idiotypic antibodies of interest will react with sera containing autoantibodies to A68, but not to sera from normal individuals lacking these autoantibodies. To screen clones that have been produced using monoclonal antibodies as the initial antigen, essentially the same strategy is utilized with the exception that a direct ELISA is used. In this instance, the monoclonal antibody that was used as the immunogen is modified to a F(ab')$_2$ fragment and is conjugated to HRP. This methodology is necessary so that the monoclonal antibody used to detect the anti-idiotypic antibody is not captured by the anti-mouse Fc antibody on the plate.

Further characterization of the anti-idiotypic monoclonal antibodies is accomplished by use of a competition assay with A68. These assays are performed by adding the anti-idiotypic antibody to the plate as described above. Then, detection antibodies (either human serum antibodies or monoclonal F(ab')$_2$ HRP conjugated antibodies) are added together with various concentrations of A68. A68 will compete with the anti-idiotypic antibodies for the antigen recognition site on the detection antibody resulting in a diminution of signal.

It should be noted that there are several variations of the above assay that also could be used to screen for anti-idiotypic antibodies. These assays are obvious to those skilled in the art.

Example 7

Phosphorylated Recombinant Tau and Treatment with Hypericin

This Example describes the means by which recombinant human tau (rht) can be phosphorylated and optionally treated with hypericin to increase its reactivity with Alzheimer's disease autoantibodies.

For these studies, a MSN extract was prepared by culturing MSN cells (Reynolds et al., *J. Natl. Cancer Inst.*, 76: pp. 375–387, 1986) in T225 flasks in RPMI 1640 (supplemented with 15% fetal bovine serum, 100 U/ml penicillin, 100 ug/ml streptomycin) in a humidified incubator with a 5% $CO_2$ atmosphere. The cells were collected when 80% confluent by scraping and transferred into 50 ml conical test tubes. Cells were pelleted by centrifugation at 2,000×G, for 5 minutes, 21° C. and the cell pellet was washed with TBS. Then, two volumes of P2 buffer (20 mM HEPES, pH 7.2, 20 mM KCl, 1 mM dithiothreitol, 2.5 µg/ml each of leupeptin, pepstatin, aprotinin, 10 µg/ml aPMSF, 0.5 mM EDTA) were added, and the cell pellet was homogenized on ice with a glass-Teflon Dounce homogenizer. The homogenate was sedimented at 8,000×g for 10 minutes at 4° C., and the supernatant was resedimented at 100,000×g for 60 minutes at 4° C. The resulting pellet was resuspended to 5 mg/ml in P2 buffer. Phospho-rht was used as is, or optionally, was phosphorylated to obtain phospho-rht. Phospho-rht was obtained by combining rht with an MSN extract (prepared as described above) at a concentration of 150 µg/ml each in 20 mM 4-(2-hydroxyethyl)-1-piperazine ethylenesulfonic acid (HEPES), pH 7.2, 4 mM KCl, 5 mM $MgCl_2$, 1 mM dithiothreitol, 0.5 mM ethylenediaminotetra acetic acid (EDTA), 2.5 μg/ml each of aprotinin, leupeptin, and pepstatin, 10 μg/ml 4-amidino-phenyl methylsulfonyl fluoride (a PMSF), 1 μM okadaic acid, 2 mM ATP, 1 mM ethylene glycol bis(b-aminoethylether)N,N,N,N'-tetraoacetic acid (EGTA), 10 mM phosphocreatine, and 20 μg/ml creatine phosphokinase. CyclicAMP-dependent kinase catalytic subunit (Pierce) may be included at 1.67 units per 10 μl. The reaction is initiated by the addition of the ATP, and proceeds at 30° C. for 16 hr with agitation. The reaction is stopped by addition of 2 volumes 5 mM EDTA, 20 mM 2-glycerol phosphate, 20% glycerol in BBS, pH 8.3. The phosphorylated rht may be used as is, or may be re-purified by boiling for 10 min centrifugation at 15,000×g for 10 min at 4° C., and chromatography on Ni-nitriloacetic acid agarose column as described above.

Hypericin stock was prepared at 20 mM in DMSO, and stored at −20° C. The rht or phospho-rht preparation to be treated was diluted in 20 mM $Na_2B_4O_7$, 100 mM $H_3BO_3$, 75 mM NaCl, pH 8.3 (BBS) to twice the desired assay concentration, and mixed 1:1 with 6 μM hypericin in BBS for greater than 1 hour, at 21° C. in the light (hypericin is light-sensitive). Substituting 2 to 5 μM calphostin C has a similar effect on rht and phospho-rht immunoreactivity.

Both rht and phospho-rht were treated with hypericin and analyzed for reactivity with human autoantibodies in the sandwich assay described previously. Both rht and phospho-rht were reactive with both Alzheimer's disease and control sera even without hypericin treatment, but hypericin increased the signal intensity 2- to 4-fold for rht, and about 100-fold for phospho-rht (see Table 3). This amplification of signal makes possible the use of these purified proteins as well-defined antigens for characterization and quantitation of human autoantibodies. A68 also showed reactivity with these same sera.

TABLE 3

Hypericin Effects on human serum autoantibody reaction with rht and phospho-rht

| Antigen | AD serum (Relative Light Units) | Control serum (Relative Light Units) |
| --- | --- | --- |
| rht | 70.8 | 72.4 |
| rht + hypericin | 317.6 | 170.6 |
| A68 | 58.9 | 4.6 |
| no antigen | 1.9 | 1.7 |
| phospho-rht | 4.3 | 2.4 |
| phospho-rht + hypericin | 366.1 | 227.0 |

The results depicted in Table 3 confirm the discovery of agents which cause rht or phosphorylated rht to increase their respective reactivity with A68 autoantibodies. These are useful antigens for enhanced detection of human autoantibodies in AD.

Example 8

Increasing the Reactivity of Components of Alzheimer's Disease Antigen

This example describes methods of treating agents (i.e., which constitute components of the Alzheimer's disease antigen, such as tau, phosphorylated tau, and the like) such that their condition following such treatment optimally mirrors the state in which they are present in an A68 antigen preparation according to the invention which is substantially free of immunoglobulin G. Such treatment thus provides for a method of increasing the ability of these agents to detect autoantibodies that are present in Alzheimer's disease.

For instance, preferably according to the invention, it is possible to use for the detection of Alzheimer's disease autoantibodies recombinant human tau (rht) that has been treated so that it will function in a similar fashion as an Alzheimer's disease antigen. One such method comprises phosphorylation of rdt, desirably by using a cell extract prepared from neuroblastoma cells (e.g., MSN neuroblastoma cells) that have been optionally treated with okadaic acid (OKA) which increases the cell extract's ability to hyperphosphorylate rht. Hyperphosphorylated tau is a major component of Protein A/G treated A68. The hyperphosphorylated rht produced by such treatment desirably can also be used as an Alzheimer's disease antigen to detect human autoantibodies in serum.

Similarly, rht and/or phosphorylated rht (as detailed above) optimally can be treated with hypericin (or calphostin C) to produce an Alzheimer's disease antigen suitable to detect autoantibodies diagnostic for Alzheimer's disease. Thus, hypericin (or calphostin C) treated rht desirably can be employed according to the invention as a suitable Alzheimer's disease antigen that can be used to detect autoantibodies diagnostic for Alzheimer's disease.

Also, rht optionally can be treated with free fatty acids (FFA), according to Wilson and Binder (Am. J. Path, 150, (6), pp. 2181–95 (1997); J. Biol. Chem., 270, (41), pp. 24306–14, (1995)). Such treatment, preferably using unsaturated fatty acids (e.g., including but not limited to oleic or linoleic acids, most preferably arachidonic acid) results in the polymerization of the rht, which polymerization also is a characteristic of Protein A/G treated A68. Thus, FFA treated rht is a suitable Alzheimer's disease antigen that can be used to detect autoantibodies diagnostic for Alzheimer's disease.

Moreover, it will be clear to one skilled in the art that use of purified or partially purifies kinases which have been associated in the literature with tau phosphorylation either singly or in combination can produce hyperphosphorylated rht or hyperphosphorylated isolated normal tau suitable as an Alzheimer's disease antigen to detect autoantibodies diagnostic for Alzheimer's disease. Such kinases include, but are not limited to, PKA, GSK, cdc2, cdc25, casein kinase I and II, MAP kinase, and PHF kinase.

In still another manifestation of the invention, it has been described by Smith, Sayer, Monnier, Perry, et al. (Trends in Neuroscience, 18, (4), pp. 172–6, (1995); Proc. Natl. Acad. Sci. USA, 91, pp. 5710–14, (1994); Ann. NY Acad. Sci., 738, pp. 447–54, (1994)), that advanced glycation endproducts (AGEs) result in the crosslinking of tau via the Maillard reaction and Amadori rearrangement. There is evidence of this crosslinked tau in neurofibrillary tangles which, as previously indicated, are comprised of A68/hyperphosphorylated tau. Thus, preferably treatment of rht using the lipid peroxidation product 4-hydroxy-2-nonenal (HNE) or other AGEs either alone, or in combination, produces an Alzheimer's disease antigen suitable for the detection of autoantibodies diagnostic for Alzheimer's disease.

These methods thus can be employed to increase the ability of an Alzheimer's disease antigen (i.e., isolated components of the antigen) to detect autoantibodies that are present in Alzheimer's disease.

Example 9

Purification of Bovine Tau

This Example describes the purification of bovine tau.

Bovine brains are obtained as soon after slaughter as possible and placed in ice water. All subsequent steps are at 4° C. unless otherwise indicated. Large blood clots are removed from 600 gms cerebral cortex. The overlying meninges may be removed as well. 2-mercaptoethanol and PMSF is added to 900 ml 0.1 M 1,4-piperazinediethanesulfonic acid (PIPES)-NaOH, pH 6.6, 1 mM EGTA, 1 mM $MgSO_4$ (PEM) to a final concentration of 1 mM each, and the brains are placed therein. The brains are homogenized using a Waring blender for 4 seconds at low speed, then 4 seconds at medium speed. The homogenate is subjected to centrifugation at 23,000×g for 90 minutes at 2° C., and the supernatant is carefully collected. GTP is added to the supernatant to a final concentration of 1.0 mM. Alternatively, GTP can be added to 0.1 mM, and ATP can be added to 2.5 mM. Incubation at 37° C. with gentle swirling is performed for 30 minutes in a large flask to assemble microtubules. The supernatant is then transferred to centrifuge bottles underlayed with 20 ml 10% sucrose in PEM containing 1 mM GTP, and subjected to centrifugation at 37° C. for 45 minutes at 23,000×g. The supernatant is discarded, the pellet is resuspended in 75 ml PEM containing 1 mM GTP at 0° C., and homogenized with a teflon/glass homogenizer (2 passes at 2000 rpm), and incubated on ice for 30 minutes to disassemble the microtubules. The mixture is then subjected to centrifugation at 38,000×g for 30 minutes at 2° C. The supernatant is decanted into preweighed centrifuge tubes and incubated at 37° C. for 15 minutes to repolymerize the microtubules. The tubes are then subjected to centrifugation at 38,000×g at 37° C. for 30 minutes. This pellet contains MAPs and tubulin in purified form. To separate MAPs from tubulin, the pellet is resuspended in ⅓ volume PEM containing 1 mM GTP, 1 M NaCl at 0° C. and the liquefied pellet is loaded at 0.5 ml/min, 4° C., onto a DEAE-sephadex (A-50, Pharmacia) column, 1 ml bed volume/ml pellet, which has been equilibrated in PEM containing 1 mM GTP, 0.25 M NaCl. MAPs elute in the unbound fraction, are termed MAPf. Subsequently, bovine tau is purified further from MAPf on phosphocellulose.

An alternative preparation of tau protein utilizes the first supernatant described above, but instead of assembling the microtubules, the supernatant is heated to 90° C. for 5 min. It is then subjected to centrifugation at 23,000×g for 90 min at 4° C. The tau protein is subsequently concentrated and partially purified by anion exchange chromatography on DEAE-cellulose (Whatman DE52) equilibrated in PEM. The tau protein is eluted with a linear 0–1M NaCl salt gradient, and stored at −80° C.

Example 10
Reverse ELISA sandwiches for A68 and Bovine Tau

This Example describes reverse sandwiches for A68 and bovine tau.

Autoantibodies reactive with A68 and bovine tau also can be detected in a sandwich wherein the antigen is immobilized. This is accomplished by coating Dynex Microlite 1 plates with 3 μg/ml goat anti-mouse Ig(Fc) in coat buffer for 3 hours at 24° C., and subsequently blocking with 288 μl 5% non-fat dry milk in BBS for 1 hour at 24° C. For A68 capture, monoclonal Ab PHF1 at 1 μg/ml in casein/TBS is added. For bovine tau capture, tau1 (Roche) at 1 μg/ml in casein/TBS is added. Both are incubated for 2 hours at 24° C. 1 μl A68 (about 30 ng) or 1 μl MAPf (about 100 ng bovine tau) are added in 5% fetal bovine serum (HyClone) in BBS for 20 hours at 4° C. Alternative antigens (e.g. phosphorylated rht +/− hypericin) may be utilized. Serum to be tested for autoantibodies is added to wells at 1:100 dilution in 1% non-fat dry milk, 5% normal goat serum (Sigma), BBS and incubated 16 hours at 4° C. Bound autoantibody is detected with 0.27 μg/ml horseradish peroxidase-conjugated goat anti-human Ig in casein/TBS for 2 hours at 24° C. followed by addition of 90 μl LumiGlo (Kirkegaard and Perry) chemiluminescent substrate.

Chemiluminescence is measured as described above. In between each step, wells are washed with 0.1% Tween-20, tbs. All incubations are 100 μl except where indicated.

Example 11
Use of Bovine MAPf and Tau in Conjunction with A68 in Western Blot Analysis This Example describes the use of Bovine MAPf in conjunction with A68 in Western blot analysis of sera.

Bovine MAPf contains, among other things, 70% MAPs 1 & 2, 20% other MAPs, and 10% Tau MAP isoforms. The current invention, as described here, makes use of the six Tau MAP isoforms that migrate in the 40–65 kD range on a 10% SDS polyacrlyamide gel. The methods for electrophoresis, Western transfer, sera incubation, and detection of bound autoantibody are identical to the methods described previously in Example 3. The exception in this Example is the use of alternating lanes of A68 and MAPf for electrophoresis. MAPf is used at the concentration of 1.5 ug total protein/lane. Patient sera is incubated with the strips of nitrocellulose containing purified A68 protein preparation and strips of nitrocellulose containing MAPf, and bound autoantibodies are then visualized as previously described. Bound autoantibodies to purified A68 protein preparation and the tau isoforms in MAPf are then quantified using a transmittance densitometer (Bio-Rad GS-670) and Molecular Analyst Image Analysis Software (Bio-Rad Version 1.1.1). After acquiring an image of the Western blot using the densitometer, the software program is used to create a one-dimensional profile of the band patterns produced by the sera on purified A68 protein preparation and tau isoforms of MAPf. The profiles are then background subtracted. The resulting profiles contain peaks that represent both the width of the band as well as the optical density (OD) of bound antibodies. Integration of the area under the peak provides a numerical measure of bound antibodies in units of OD×mm.

Two methods of analysis are currently used to assign a diagnosis to each serum tested. In the first method, the total OD×mm signal from purified A68 protein preparation is divided by the total OD×mm signal from the tau isoforms. The sample is assigned the diagnosis of AD, or non-AD based on this ratio.

The second method takes into account not only optical density measurements, but also the number of MAPf tau isoforms identified by a given serum. In this method of analysis, if a bovine MAPf tau signal is present in conjunction with purified A68 protein preparation, the sample is assigned a diagnosis of AD if the tau signal contains less than three isoforms, and a diagnosis of non-AD if the sample identifies 3 or more isoforms of tau. As well, the sample is classified as non-AD if it lacks purified A68 protein preparation signal, regardless of the number of tau bands. Quantification of the MAPf tau signal in this instance takes on the formula: (sum OD×(n−2)). For this formula, "Sum OD" is the sum of OD×mm measurements of all tau isoforms and "n" is the total number of bands present of the six tau MAPf isoforms. Thus, samples that give a purified A68 protein preparation signal and lack a substantial tau signal are termed AD, all other combinations (A68 signal+tau signal, tau signal alone, or absence of both signals) are diagnosed as non-AD.

The use of tau isoforms is not limited here to Bovine tau isoforms found in MAPf. Other forms of tau protein may be used such as tau purified from brain and recombinant tau either as a single molecule or as a mixture of tau isoforms. Additionally, the invention is not limited to Bovine tau. Purified tau or MAP from brains or cultured cells of other species may be used such as human, rodent, or other mammalian sources as well as preparations from avian and reptiles.

Example 12
Indirect ELISA on Nitrocellulose Plates

This Example describes an indirect ELISA on nitrocellulose plates.

Autoantibodies reactive with purified A68 protein preparation and bovine tau may also be detected in an indirect ELISA assay wherein the antigen is immobilized in a microtiter plate in which the bottom of each well is nitrocellulose. This support allows the antigen to be displayed in a manner which more closely resembles the Western blot than does a polystyrene support. Millipore MHAB plates are pre-wet with BBS for 1 minute, then the buffer is drawn through the filter under vacuum. Antigen is applied to the wells in BBS at 0.01 to 10 μl per well (0.3 to 300 ng), and allowed to bind for 3 hours at 24° C. In these experiments, the antigen may be purified A68 protein preparation, bovine tau (MAPf), or purified A68 protein preparation analogues such as phosphorylated rht. The antigen solution is drawn through the filter under vacuum, and the filters are blocked with 5% non-fat dry milk in BBS for 1.5 hours at 24° C. Subsequently, all incubation solutions are removed by a plate washer (Nunc) and washed with 0.1% Tween 20 in TBS rather than by drawing through the membrane under vacuum. 1% serum is added to wells in 100 μl of 1% non-fat dry milk, 5% normal goat serum, BBS, and incubated for 16 hours at 4° C. Bound human Ig is detected by addition of HRP-conjugated goat anti-human Ig in 1% casein/TBS for 2 hours at 24° C. followed by addition of 90 μl LumiGlo (Kirkegaard and Perry) chemiluminescent substrate. Chemiluminescence is measured as described above.

All of the references cited herein are hereby incorporated in their entireties by reference. In particular, the entire text and teachings of PCT International Application WO 96/20218 is hereby incorporated by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A method for detecting autoantibodies that are present in Alzheimer's disease comprising:
    (a) obtaining a protein preparation consisting essentially of an antigen that is immunologically reactive with a monoclonal antibody produced by the hybridoma cell line identified as ATCC No. HB9205, said preparation being substantially free of immunoglobulin G, a bovine microtubule associated protein preparation, and a sample being tested for the presence of said autoantibodies;
    (b) electrophoresing said protein preparation and said bovine microtubule associated protein preparation on separate lanes on a gel;
    (c) transferring said electrophoresed protein preparation and said bovine microtubule associated protein preparation to a membrane;
    (d) contacting said membrane with a sample being tested for the presence of said autoantibodies such that an autoantibody complex can form with antigen present in said protein preparation and/or with antigen present in said bovine microtubule associated protein preparation; and
    (e) detecting said autoantibodies by the formation of said complex(es).

2. A method for detecting autoantibodies that are present in Alzheimers disease comprising:
    (a) obtaining a protein preparation consisting essentially of an antigen that is immunologically reactive with a monoclonal antibody produced by the hybridoma cell line identified as ATCC No. HB9205, said preparation being substantially free of immunoglobulin G and a bovine microtubule associated protein preparation;
    (b) contacting said protein preparation and said bovine microtubule associated protein preparation with a sample being tested for the presence of said autoantibodies such that an antigen-autoantibody complex can form; and
    (c) detecting said autoantibodies by the formation of said complex.

3. The method of claim 2, wherein the amount of said complex is measured, and the amount of said autoantibodies is determined by the amount of said complex.

4. The method of claim 2, wherein said sample is selected from the group consisting of cerebrospinal fluid, brain tissue homogenate/extract, urine, and blood.

5. The method of claim 2, wherein said protein preparation or bovine microtubule associated protein preparation is attached to a solid matrix.

* * * * *